United States Patent
Patel et al.

(10) Patent No.: US 11,574,075 B2
(45) Date of Patent: Feb. 7, 2023

(54) DISTRIBUTED MACHINE LEARNING TECHNIQUE USED FOR DATA ANALYSIS AND DATA COMPUTATION IN DISTRIBUTED ENVIRONMENT

(71) Applicant: MEDICAL INFORMATICS CORPORATION, Houston, TX (US)

(72) Inventors: Raajen Patel, Houston, TX (US); Vincent Gagne, Bellaire, TX (US); Christian Pesantes, Houston, TX (US)

(73) Assignee: Medical Informatics Corp., Houston, TX (US)

(*) Notice: Subject to any disclaimer, the term of this patent is extended or adjusted under 35 U.S.C. 154(b) by 850 days.

(21) Appl. No.: 16/432,712

(22) Filed: Jun. 5, 2019

(65) Prior Publication Data
US 2019/0370490 A1    Dec. 5, 2019

Related U.S. Application Data

(60) Provisional application No. 62/680,705, filed on Jun. 5, 2018.

(51) Int. Cl.
| | |
|---|---|
| G06F 21/62 | (2013.01) |
| G06N 20/00 | (2019.01) |
| G06F 16/2458 | (2019.01) |
| G16H 10/20 | (2018.01) |
| G06F 9/48 | (2006.01) |

(52) U.S. Cl.
CPC ........ *G06F 21/6245* (2013.01); *G06F 9/4881* (2013.01); *G06F 16/2471* (2019.01); *G06N 20/00* (2019.01); *G16H 10/20* (2018.01)

(58) Field of Classification Search
CPC .......... G06F 21/6245; G06F 16/2471; G06F 9/4881; G16H 10/20; G06N 20/00
USPC .................................... 726/1–12; 706/45–50
See application file for complete search history.

(56) References Cited

U.S. PATENT DOCUMENTS

| | | | |
|---|---|---|---|
| 1,055,737 A * | 3/1913 | Gilbert ...................... | B03B 5/24 209/494 |
| 8,499,010 B2 * | 7/2013 | Gracie ................ | G06F 12/0261 711/171 |
| 8,548,828 B1 * | 10/2013 | Longmire .............. | G16H 40/67 706/45 |

(Continued)

OTHER PUBLICATIONS

Bao et al, "Online Job Scheduling in Distributed Machine Learning Clusters", IEEE, pp. 495-503 (Year: 2018).*

(Continued)

*Primary Examiner* — Anil Khatri
(74) *Attorney, Agent, or Firm* — Schafer IP Law

(57) ABSTRACT

A system for distributed computing allows researchers performing analysis on data having legal or policy restrictions on movement of the data to perform the analysis on data at multiple sites without exporting the restricted data from each site. A primary system determines which sites contain the data to be executed by a compute job and sends the compute job to the associated site. Resulting calculated data can be exported to a primary collecting and recording system. The system allows the rapid development of analysis code for the compute jobs that can be executed on a local data set then passed to the primary system for distributed machine learning on the multiple sites without any changes to the code of the compute job.

11 Claims, 6 Drawing Sheets

(56) References Cited

U.S. PATENT DOCUMENTS

| | | | | |
|---|---|---|---|---|
| 8,655,817 | B2* | 2/2014 | Hasey | A61B 5/00 706/45 |
| 9,339,188 | B2* | 5/2016 | Proud | H04W 4/70 |
| 9,996,670 | B2* | 6/2018 | Dejori | G16H 50/70 |
| 10,262,271 | B1* | 4/2019 | Doddi | G06N 5/022 |
| 10,540,606 | B2* | 1/2020 | Dirac | G06N 20/00 |
| 10,713,589 | B1* | 7/2020 | Zarandioon | G06N 20/20 |
| 10,878,361 | B2* | 12/2020 | Tanwir | G06F 3/0481 |
| 10,983,963 | B1* | 4/2021 | Venkatasubramanian | G06F 16/182 |
| 11,120,368 | B2* | 9/2021 | Varadarajan | G06N 20/20 |
| 11,164,093 | B1* | 11/2021 | Zappella | G06N 5/045 |
| 11,182,691 | B1* | 11/2021 | Zhang | G06N 20/00 |
| 11,194,775 | B2* | 12/2021 | Mishra | G06F 16/2455 |
| 11,257,574 | B1* | 2/2022 | Boussios | G06N 5/022 |
| 11,416,369 | B1* | 8/2022 | Trapani | H04L 43/0817 |
| 11,494,246 | B1* | 11/2022 | Adams | H04L 63/08 |
| 2017/0300648 | A1* | 10/2017 | Charlap | G16B 20/00 |

OTHER PUBLICATIONS

Zhang et al, "SLAQ: Quality-Driven Scheduling for Distributed Machine Learning", ACM, pp. 390-404 (Year: 2017).*

Plagianakos et al, "Distributed computing methodology for training neural networks in an image-guided diagnostic application", Computer Methods and Programs in Biomedicine, pp. 228-235 www.intl.elsevierhealth.com/journals/cmpb (Year: 2006).*

Roh et al, "A Survey on Data Collection for Machine Learning: A Big Data—AI Integration Perspective", IEEE, pp. 1328-1347 (Year: 2021).*

Jo et al, "Lessons from Archives: Strategies for Collecting Sociocultural Data in Machine Learning", ACM, pp. 306-316 (Year: 2020).*

Whang et al, "Data Collection and Quality Challenges for Deep Learning", ACM, pp. 3429-3432 (Year: 2020).*

Hohman et al, "Understanding and Visualizing Data Iteration in Machine Learning", ACM, pp. 1-13 (Year: 2020).*

* cited by examiner

DISTRIBUTED MACHINE LEARNING TECHNIQUE USED FOR DATA ANALYSIS AND DATA COMPUTATION IN DISTRIBUTED ENVIRONMENT

TECHNICAL FIELD

The present invention relates to the field of data analysis, and in particular to techniques for creating research results using large, federated, and protected data sets and distributed machine learning.

BACKGROUND ART

The process for gathering the high-resolution data for clinical research is manual and tedious. It can take months—or even years—to gather, process, and analyze it. Often times multiple legal agreements are necessary to move data from one location to another for analysis due to medical regulations surrounding patient data. This creates substantial delays in grant applications and journal publications, and sometimes means that the research project itself is not feasible to conduct, preventing the advancement of scientific development. In addition, even after a research project is completed, translating results into clinical practice has been extremely difficult.

Because the physiological data needed for clinical research typically contains personal health information (PHI), there are legal restrictions on access and portability of the PHI data that make use of that data for clinical research difficult. Existing distributed machine learning techniques have required the ability to move the underlying data in ways that are prohibited with PHI data, making them difficult to apply to large-scale, cross-institutional, medical data sets without extensive manual efforts for overcoming these administrative and regulatory barriers.

BRIEF DESCRIPTION OF DRAWINGS

The accompanying drawings, which are incorporated in and constitute a part of this specification, illustrate an implementation of apparatus and methods consistent with the present invention and, together with the detailed description, serve to explain advantages and principles consistent with the invention. In the drawings.

DESCRIPTION OF EMBODIMENTS

Figure 1:
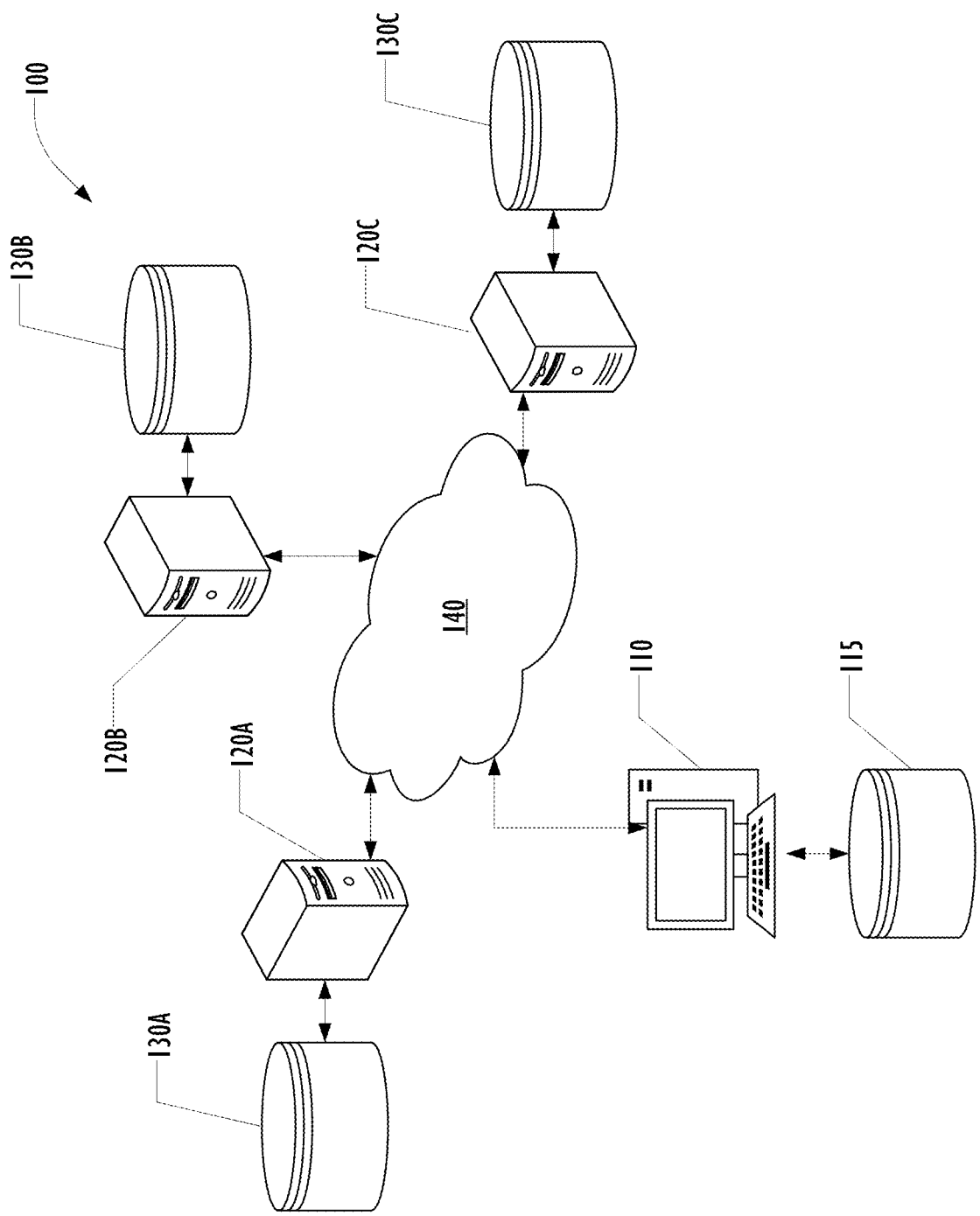
FIG. 1 is a block diagram illustrating portions of a distributed platform for performing rapid research in a healthcare environment according to one embodiment.

In the following description, for purposes of explanation, numerous specific details are set forth in order to provide a thorough understanding of the invention. It will be apparent, however, to one skilled in the art that the invention may be practiced without these specific details. In other instances, structure and devices are shown in block diagram form in order to avoid obscuring the invention. References to numbers without subscripts are understood to reference all instance of subscripts corresponding to the referenced number. Moreover, the language used in this disclosure has been principally selected for readability and instructional purposes, and may not have been selected to delineate or circumscribe the inventive subject matter, resort to the claims being necessary to determine such inventive subject matter. Reference in the specification to "one embodiment" or to "an embodiment" means that a particular feature, structure, or characteristic described in connection with the embodiments is included in at least one embodiment of the invention, and multiple references to "one embodiment" or "an embodiment" should not be understood as necessarily all referring to the same embodiment.

Although some of the following description is written in terms that relate to software or firmware, embodiments can implement the features and functionality described herein in software, firmware, or hardware as desired, including any combination of software, firmware, and hardware. References to daemons, drivers, engines, modules, or routines should not be considered as suggesting a limitation of the embodiment to any type of implementation.

Rapid Research changes the way that physiologic data processing algorithms can be created and deployed at scale across multiple institutions. Rapid Research automatically captures ALL high-resolution physiologic data and vitals from networked and non-networked devices as well as patient administration (ADT) data, labs, and meds, and transforms it into a dashboard to enable rapid production of algorithms for advancing clinical research projects. Rapid Research gives researchers the tool they need to go from idea to publication in a day, greatly increasing research output and decreasing development and deployment time. It also enables the ability to then take that research algorithm and create a software based predictive monitor that can be deployed in clinical practice along with contextual alerts and smart alarms to improve care and outcomes, as well as scale this to other clinical organizations. Rapid Research also allows researchers to:

(1) Get seamless, real-time collection of high-resolution physiological data from networked and non-networked devices;

(2) Tie in labs and medications for full clinical picture; and (3) Give any user access so they can quickly and easily: (a) Study and compare cohorts of patients; (b) Review and tag clinical events; (c) Run pre-defined or custom analyses; and (d) Perform large-scale data analytics.

Embodiments of Rapid Research provide open APIs for the MATLAB® and C programming languages. (MATLAB is a registered trademark of The Mathworks, Inc.) Rapid Research can be implemented on a scalable, flexible platform that enables the deployment of the researcher's algorithm into clinical practice.

There are four steps that are necessary and sufficient for developing predictive algorithms in a clinical research environment:

1. Rapid prototyping—this is the small-scale analysis of a small amount of data. This is typically done using the MATLAB, PYTHON®, or C programming languages. Other programming languages can be used. (PYTHON is a registered trademark of the Python Software Foundation.)

2. Large scale retrospective analysis—once a prototype algorithm is created (from step 1) it needs to be applied to all of the data collected from a given study population. This often requires parallel processing to be computationally feasible.

3. Distributed machine learning—once the retrospective analysis is done, there is the need to fuse clinical features together into a single trained and validated model using machine learning.

4. Prospective real-time evaluation—once a model has been developed, it needs to be applied to patients for real-time evaluation of their data.

Each of these steps is described in more detail below. An underlying infrastructure enables collecting, archiving, and processing patient physiological data and provides the ability to perform research on that data. In one embodiment, the infrastructure is provided by the SICKBAY™ platform of Medical Informatics Corp., the assignee of the current application. (SICKBAY is a trademark of Medical Informatics Corp.) An application programming interface (API) provided by the SICKBAY platform allows the researcher to generate code quickly in MATLAB, C, or some other programming language, then test the code on a small set of locally available data.

During this rapid prototyping step, the researcher may, for example, take raw measurements of up to 12 hours of data, write code in MATLAB to process that data, then execute the prototype on the data to generate new features and visualize the features on top of the measured data. Depending on the results, the researcher may then cycle through modifying the code, executing the code on the data, and reviewing the results until satisfied with the new feature.

By prototyping the code in MATLAB or some other programming environment supported by the SICKBAY API, the researcher is able to rapidly change the code to see the application of the new feature. The SICKBAY API abstracts a lot of functionality of the hospital infrastructure system, making access to local data easy from the researcher's prototype code, and making it portable across institutions.

The SICKBAY API then allows the researcher to take the code developed locally on the researcher's computer and, without changing a single line of the researcher's code, distribute the code to all of the informatics servers on the SICKBAY system, execute the researcher's code on large scale retrospective data held by the SICKBAY system in parallel, with each informatics server executing the code independently of each other. Thus, the researcher can develop locally and execute globally.

This large-scale retrospective data analysis allows the researcher to develop the new feature on the large-scale retrospective data and see the results in a researcher interface.

As used herein, the term "feature" refers to physiological data that is a portion or segment of a larger collection of related data that can be extracted and used as a separate measurement. For example, an electrocardiogram (ECG) data stream contains several segments, e.g., ST segment, Q wave, R wave, T wave, TQ interval, etc. Each of those segments can be used as a feature separately from the ECG data stream as a whole. Thus, for example, the ST segment could be extracted from the ECG data stream and used as a new feature.

Once the researcher has a collection of features that the researcher wants to consider for a new measure, such as a predictive value, the researcher may combine the features. In some embodiments, a weighting scheme may be used for matching the features to a classification scheme. Some features may be used as control features while other features may be used as study features in this step.

Once the new measure has been developed as described above, the researcher may use the same code for distributed machine learning on not just the original SICKBAY system, but on other SICKBAY systems in use at other hospitals or research facilities.

FIG. 1 is a block diagram illustrating portions of a distributed platform 100 for performing rapid research in a healthcare environment according to one embodiment. Other elements of the platform, including elements used for collecting healthcare data from patients are omitted for clarity of the drawing.

In this example platform 100, a researcher begins by developing code to analyze data using locally available data in a local database 115 on a researcher computing system 110. After performing machine learning on the local data using the code, the researcher may use functionality such as an API built into the distributed platform for distributing the code to a plurality of informatics servers 120A, 120B, 120C, each of which has access to a corresponding database 130A, 130B, 130C. A network 140 connects the various computer systems of platform 100.

Although only three informatics servers 120A, 120B, 120C are illustrated in FIG. 1 for clarity, any number of informatics servers can be provisioned. Although illustrated as a single network 140, a collection of interconnected networks may provide network connectivity across the platform 100. Although described as a database, any form and technique of data storage accessible to the informatics servers 120A, 120B, 120C may be used.

The code received from the researcher computing system 110 may then be executed by the informatics servers 120A, 120B, 120C without change, allowing a larger scale distributed machine learning procedure to be performed using the code and the data in databases 130A, 130B, 130C. Because the platform 100 is maintained within a single healthcare environment, data containing PHI may be moved around the platform 100 if desired, subject to local policies for handline PHI as well as regulatory and statutory constraints on the use of PHI.

Machine learning is typically done in one of two ways:

(1) everything is done locally, on local data. This constrains the kinds of problems that can be solved, because the availability and amount of data is limited. Even though the researcher may have larger amounts of data in the platform 100 than in the researcher computing system 110, non-local data may be valuable for performing machine learning.

(2) machine learning is done on a distributed network of servers, where the data to be analyzed is distributed across multiple machines. The conventional technique for such distributed machine learning relies on an underlying file system, typically the Hadoop® Distributed File System (HDFS™), which is a scalable fault tolerant, cost efficient storage system for big data. The HDFS file system is a Java®-based file system developed by The Apache Software Foundation. (HADOOP is a registered trademark of The Apache Software Foundation. HDFS is a trademark of The Apache Software Foundation. JAVA is a registered trademark of Oracle America, Inc.)

While HDFS file systems have advantages in many settings, there are weaknesses that make HDFS file systems undesirable in working with patient physiological data. One weakness is the difficulty in mapping from a standard (non-HDFS) file system, such as a Windows® file system. Another weakness is the difficulty in working with PHI data, where data security requirements may make HDFS file systems unacceptable. Specifically, HDFS file systems do not have the ability to prevent a file from being moved from one location to another, which would violate medical regulations for the protection of patient data. As a result, while a single institution may run a HDFS system to preform data analysis, there is currently no federated, cross-institution, infrastructure for preforming distributed data analysis on protected health data.

The Apache Software Foundation has developed SPARK™, an open: source fast and general compute engine for Hadoop data, typically using an HDFS file system. (SPARK is a trademark of the Apache Software Foundation.) The SPARK engine provides a simple and expressive programming model that supports a wide variety of applications, including extract, transform, and load (ETL) processes for extracting data from multiple data sources, machine learning, stream processing, and graph computation.

Although the SPARK engine was designed for running with the HDFS file system, by removing the portions of the SPARK engine that are responsible for operating with the HDFS file system and mapping the SPARK engine infrastructure to the SICKBAY distributed file system, a SPARK system can be run without the complexity of the HDFS file system. This modified SPARK system can then interact directly with the native distributed file system of the SICKBAY platform.

Figure 2:
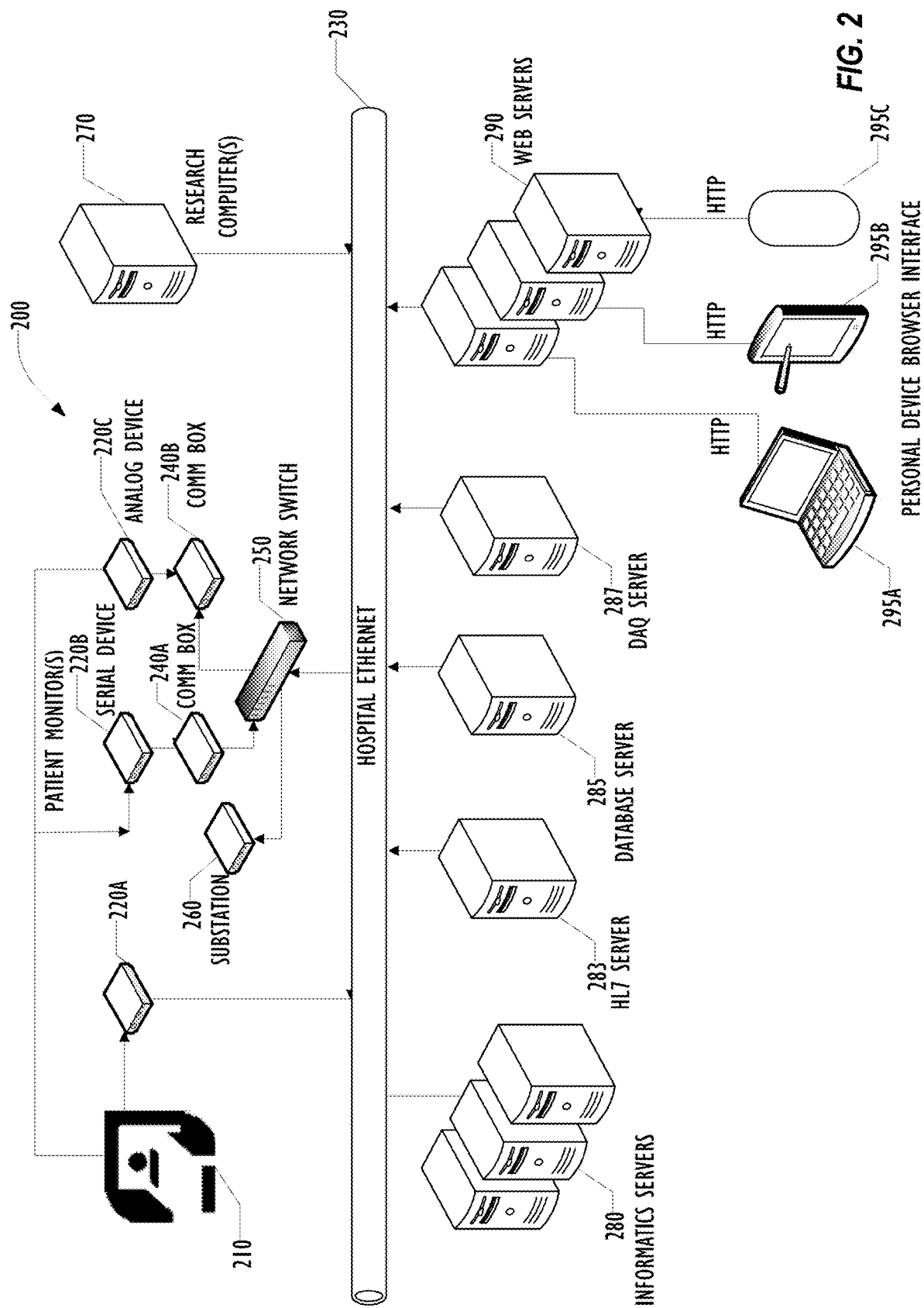
FIG. 2 is a block diagram illustrating a distributed grid-computing platform for collecting, archiving, and processing arbitrary data in a healthcare environment according to one embodiment.

FIG. 2 is a block diagram illustrating a SICKBAY platform 200 for collecting, archiving, and processing arbitrary data in a healthcare environment that can provide an environment for rapid research using distributed machine learning according to one embodiment. More information about the platform 200 can be found in "Distributed Grid-Computing Platform for Collecting, Archiving, and Processing Arbitrary Data in a Healthcare Environment," U.S. Pat. Pub. No. 2015/0142475A1, filed Nov. 20, 2014 and published May 21, 2015, which is incorporated herein in its entirety for all purposes.

As illustrated, there are five types of servers: the data acquisition (DAQ) server 287, the informatics server(s) 280, the database server 285, the Health Level 7 (HL7) server 283, and the web server(s) 290. Any number of any of the types of servers may be deployed as desired. All of the servers 280-290 connect to each other and the bedside monitors via one or more hospital networks 230. Although illustrated as a single hospital Ethernet network 230, any number of interconnected networks may be used, using any desired networking protocols and techniques.

Also connected to the hospital network 230 are a number of bedside monitors for monitoring physiological data for a patient in bed 210. These bedside monitors may include network connected monitors 220A, which can deliver digital physiological data to the hospital network 230, serial devices 220B, which produce digital data but are not directly connected to a network, and analog devices 220C, which produce analog data and are not directly connected to a network. Communication boxes 240A and 240B allow connecting the serial devices 220B and analog devices 220C, respectively, to the hospital network 230, typically through a network switch 250. In addition, a substation 260 may be also connected to the network 230 via the network switch 250 for performing data manipulation and time synchronization as described below. Any number of bedside monitors 220 may be used as determined advisable by physicians and other clinical staff for the patient in bed 210.

Although as illustrated in FIG. 2 the bedside monitors and associated communication devices are connected directly or indirectly to the hospital network 230, remote bedside monitoring devices may be used as part of the system 200, such as home monitoring devices, connected to the hospital network 230 indirectly through the Internet or through other communication techniques.

Additionally, one or more research computers 270 may be connected, directly or indirectly, to the hospital network 230, allowing researchers to access aggregated data collected from bedside monitors 220 for performing analytics and development.

The database server 285 is configured for storage of historical patient data databases, which can be connected to a historical patient data graphical interface for displaying historical patient data.

The web servers 290 are configured for communicating with personal devices such as laptop 295A, tablet 295B, or smart phone 295C via a web browser interface using HyperText Transport Protocol (HTTP).

The storage system of the SICKBAY platform 200 is a collection of files stored on a collection of computers. The SICKBAY platform 200 has metadata about what each file means and its location in the SICKBAY platform 200, such as an IP address of the informatics server 280 storing the file. Unlike conventional distributed machine learning platforms, in which the data has to be copied from local file systems to a cloud-based or network file system such as the HDFS file system, in the SICKBAY platform 200, the data can stay in place (i.e. the data stays within the institution that recorded it, rather than being shipped to the cloud for central aggregation) and be worked on in place by code distributed to each of the Sickbay informatics servers 280.

The HADOOP filesystem was created to ensure that every potential CPU that is available, has maximum utilization. If a CPU is not utilized, then data will be copied from one server to another, to allow that CPU to be effective. However, this model is ineffective when the data is not allowed to be moved by policy. In these cases, maximizing CPU utilization is less important than simply completing the calculation (albeit slower) across all of the restricted data. As a result, a new model is required which, while less computationally efficient, complies with medical regulations which prevent the free transport of personal data. As a result, we create a new way of performing distributed machine learning, which utilizes a hierarchal approach, where only aggregated (i.e. non-PHI data) is computationally manipulated at the top level of the hierarchy (which is cloud-based), while the low-level compute operations are performed at the site where the data was collected. This hierarchical and distributed structure for data analysis and machine learning resolves all of the associated PHI issues, by preventing the movement of data across institutional boundaries, allowing large-scale, cross-institutional, analysis of patient data to be executed.

In a single organization, a researcher could put files on a collection of servers, then put the SICKBAY-SPARK system on top and do machine learning without an HDFS file system and without changing the way the files are stored. This is the platform 100 of FIG. 1. But an abstraction of the SICKBAY system allows running a SPARK primary system in a cloud that connects to multiple SICKBAY-SPARK systems across multiple organizations, each of which has rules that limit how data can be transferred out of the organization, generally by prohibiting such movement.

In such a scenario, data cannot move out of the individual organizations, but the researcher would prefer to use distributed machine learning on the data at multiple organizations to get more accurate results on a larger data set.

Because the SICKBAY-SPARK system can transfer the researcher's code into each organization's SICKBAY-SPARK system, the code can then operate, unchanged, on the data stored in each organization's system without violating the data protection rules of that organization, and produce non-PHI metadata that is unprotected data and can be transferred out of the organization. The non-PHI metadata from each organization can then be aggregated in the cloud.

This allows distributed machine learning across multiple organizations without moving PHI data off-premises, which is highly advantageous for secure machine learning. Previous distributed machine learning solutions have required setting up a secure cloud, moving all of the data to the secure cloud, and running something on the secure cloud-stored data. The SICKBAY-SPARK system allows doing data analysis on all of the data across multiple organizations while maintaining the privacy of each organization's data, because each organization would allow the researcher's code to be imported into their SICKBAY-Spark system to manipulate the data on their system and take out calculated data, as long as the underlying data is not exported.

Thus a network of research hospitals can each run instances of the SICKBAY-SPARK system and principal investigators at each site can generate code for analyzing the data across all the network, allowing network-wide collaboration with principal investigators at other installations and the production of research papers with joint authorship calculating features on the large data sets across the entire network, without ever needing offsite access to the underlying data.

A SPARK primary according to one embodiment is configured to know of the existence of each of the SICKBAY-SPARK systems and what data is held by each SICKBAY-SPARK system.

After researchers successfully create a new metric and feature based on the distributed machine learning exercise, the new feature should be used in real-time displays on streaming real-time physiological data to do evaluations. Traditionally, that would have required three different code bases, one in MATLAB for rapid prototyping, one in C for distributed machine learning, and one using something like IBM Streams for real-time analysis. With the embodiments disclosed herein, a single code base is used for all three stages. This is advantageous as it greatly accelerates the ability to deploy clinically valuable algorithms, as the developer only needs to code against a single API (namely the SICKBAY API).

In a research interface according to one embodiment, the rapid prototyping process allows superpositioning the calculated data in time series over the original data, creating graphs, alarms, and event tags. For visualization of time series, matching the calculated data with the original data can be useful. The researcher can select a type of event, select an analysis to be executed, and the system executes the analysis on all data associated with the event, instead of the researcher having to manually perform the analysis on each event of the desired type, then aggregate the results after completing the analysis on all of the indicated events. In one embodiment, the analysis can be performed sequentially on each event or can be performed in parallel.

In one embodiment, local data caching can be employed to allow modifying the researcher's code and re-performing the analysis without having to download the data from an informatics server to the researcher's local computer.

Implementation

The SICKBAY platform 200 employs a database of every file and its location, such as an IP address of the informatics server 280 holding the file. Each informatics server 280 holding a file typically has the complete file, although embodiments can split files across informatics servers, with the database identifying which piece of the file is on which informatics server 280. SPARK systems using the HDFS file system essentially collect all of the files together from their local system into the HDFS file system, then sends compute jobs to each server, on the assumption that each server has a piece (or can retrieve a piece) of the files it needs to process the job.

In the SICKBAY-SPARK system, all informatics servers 280 do not have access to all of the data. So instead of sending compute jobs to every server in the system, the SICKBAY SPARK job scheduler platform 200 uses the Sickbay database to determine which informatics servers 280 have the needed files and sends compute jobs to only those informatics servers 280. The SICKBAY SPARK system prevents file copying between servers.

Figure 3:
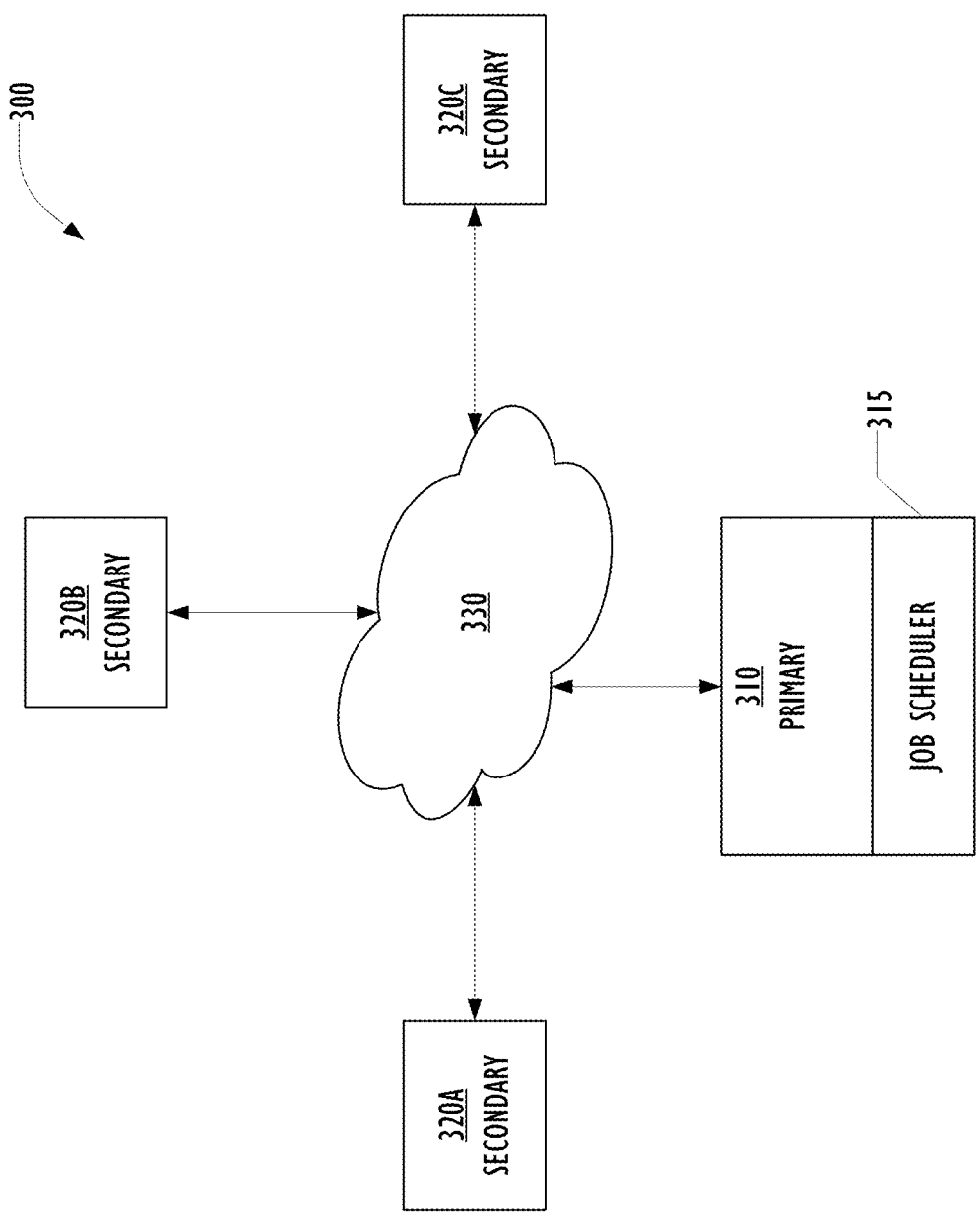
FIG. 3 is a block diagram illustrating a hierarchy of distributed computing platforms for distributed machine learning in a healthcare environment according to one embodiment.

FIG. 3 is a block diagram illustrating a hierarchy 300 of Sickbay primary and secondary systems according to one embodiment. SICKBAY primary system 310 interacts with SICKBAY secondary systems 320A, 320B, and 320C via one or more networks 330. Each of the secondary SICKBAY systems 320A, 320B, and 320C is associated with one of a plurality of organizations, each holding data that cannot be exported from the organization. Three SICKBAY secondary systems 320A, 320B, and 320C are illustrated in FIG. 3 for clarity of the drawing, but any number of SICKBAY secondary systems can be provisioned. In addition, a deeper level hierarchy of SICKBAY systems can be implemented, in which one or more of the SICKBAY secondary systems 320A, 320B, and 320C can in turn be a SICKBAY primary system connected to its own collection of SICKBAY secondary systems. Any number of hierarchy levels can be implemented as desired. For simplicity of the discussion, however, only the simple hierarchy of FIG. 3 will be described in detail.

In the abstracted configuration with a SICKBAY primary system 310 running the modified SPARK filesystem, the SICKBAY primary system 310 knows where the data resides, and a primary compute job scheduler 315 of the SICKBAY primary system 310 can send compute jobs to the SICKBAY secondary systems 320A, 320B, 320C that hold the desired data. When the compute jobs are finished, instead of sending the results back to the SICKBAY primary system 310, the SICKBAY primary system 310 may get information on whether the job has completed. In one embodiment, the results calculated by the compute jobs on each secondary SICKBAY system 320A, 320B, and 320C can stay on that system. Alternately, the results can be sent back to a primary recording data collector system separate from or part of the SICKBAY primary system 310. Because the calculated results are not PHI data, the restrictions on exporting the data out of the organization's SICKBAY system do not apply. Additional calculations can be executed on these calculated results to complete the desired computation. This allows the hierarchical SICKBAY system 300 to perform distributed machine learning on large datasets hosted by multiple organizations, even if those organizations are prohibited by policy, regulation, or statute from letting the data analyzed by the researcher's code leave the organization. Essentially, computational algorithms are automatically split into two levels: a compute layer which can be run locally against protected data, and a global compute layer which can only process un-protected data.

The SICKBAY primary system 310 knows what sites are in the network of SICKBAY-SPARK systems and what data is at each site, but does not need to know which server at any of the SICKBAY-SPARK secondary systems 320A, 320B, 320C controls the data. The SICKBAY-SPARK system 310 then manages the distribution of jobs in the SICKBAY-SPARK system 300.

Previous distributed machine learning systems used a distributed network file system such as the HDFS distributed file system, then shuffled the data around as needed to optimize the resource usage of the cluster of systems. Because that approach fails when the data cannot be moved for legal or policy reasons, the SICKBAY-SPARK system 300 provides a capability not previously available. Although the distributed hierarchical SICKBAY system 300 may sacrifice resources and efficiency by spreading across multiple SICKBAY secondary systems 320A, 320B, and 320C, the system 300 is more secure and allows access to data that cannot be accessed remotely.

Figure 4:
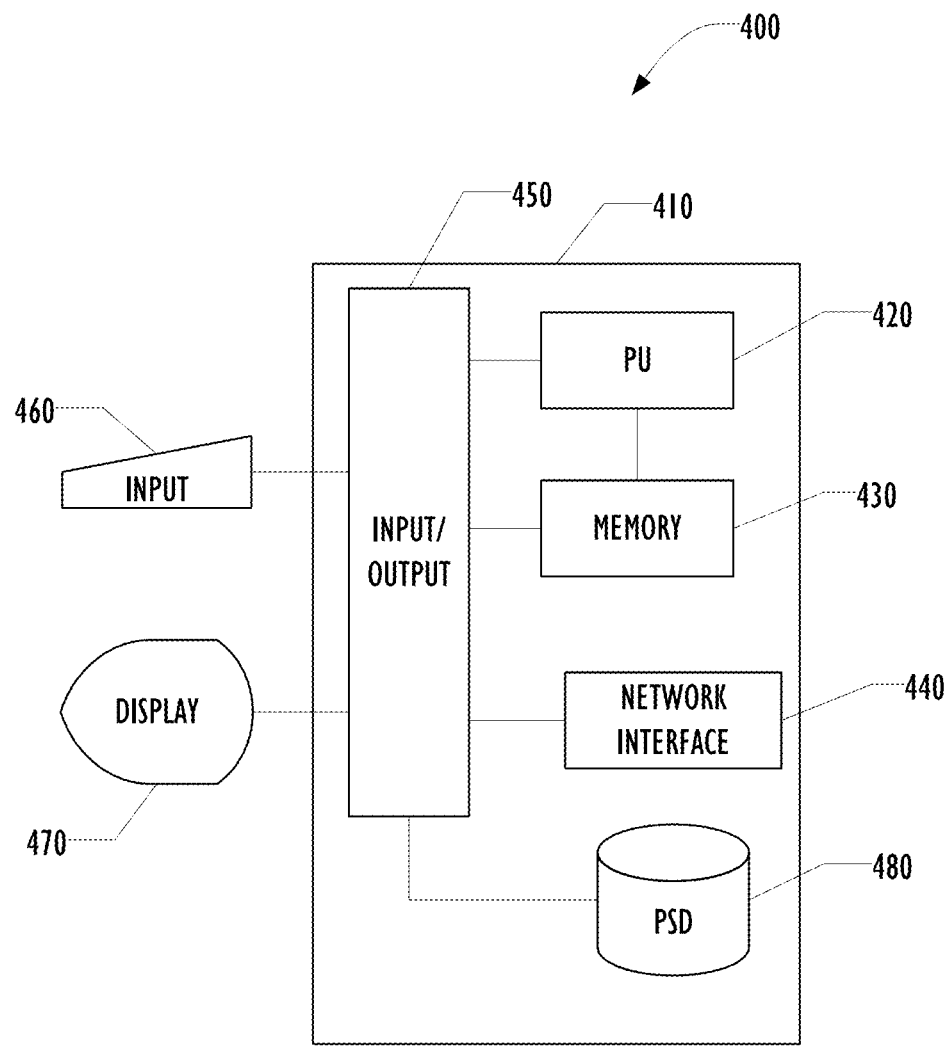
FIG. 4 is a block diagram of a computer for use in the techniques described below according to one embodiment.

The hierarchical SICKBAY 300 does not require special-purpose computing resources. Referring now to FIG. 4, an example computer 400 for use as one of the servers 280-290 is illustrated in block diagram form. Example computer 400 comprises a system unit 410 which may be optionally connected to an input device or system 460 (e.g., keyboard, mouse, touch screen, etc.) and display 470. A program storage device (PSD) 480 (sometimes referred to as a hard disc) is included with the system unit 410. Also included with system unit 410 is a network interface 440 for communication via a network with other computing and corporate infrastructure devices (not shown). Network interface 440 may be included within system unit 410 or be external to system unit 410. In either case, system unit 410 will be communicatively coupled to network interface 440. Program storage device 480 represents any form of non-volatile storage including, but not limited to, all forms of optical and magnetic, including solid-state, storage elements, including removable media, and may be included within system unit 410 or be external to system unit 410. Program storage device 480 may be used for storage of software to control system unit 410, data for use by the computer 400, or both.

System unit 410 may be programmed to perform methods in accordance with this disclosure. System unit 410 comprises a processor unit (PU) 420, input-output (I/O) interface 450 and memory 430. Processor unit 420 may include any programmable controller device, such as microprocessors available from Intel Corp. and other manufacturers. Memory 430 may include one or more memory modules and comprise random access memory (RAM), read only memory (ROM), programmable read only memory (PROM), programmable read-write memory, and solid-state memory. One of ordinary skill in the art will also recognize that PU 420 may also include some internal memory including, for example, cache memory.

Figure 5:
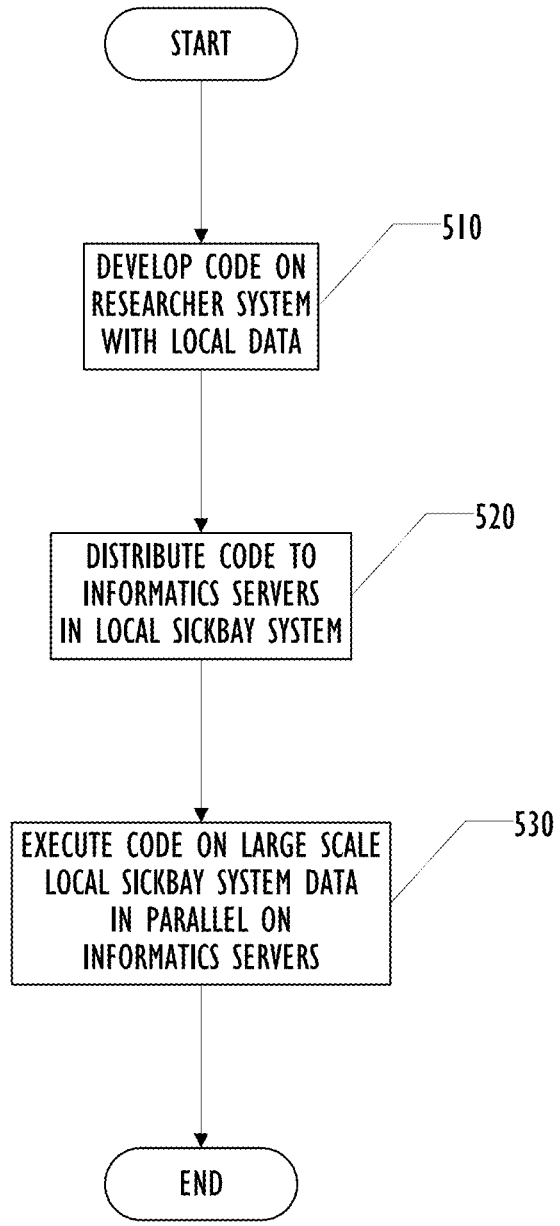
FIG. 5 is a flowchart illustrating a technique for performing rapid research in a single distributed computing platform according to one embodiment.

FIG. 5 is a flowchart illustrating a technique for distributed machine learning according to one embodiment. In this flowchart, a single SICKBAY system is used. Beginning in block 510, a researcher develops code for a feature using local data as described above. Once the researcher is satisfied with the code, the researcher may use a SICKBAY API in block 520 to distribute the code to a plurality of informatics servers in the local SICKBAY system. Distributed machine learning may then take place by running the unchanged code in block 530 on the informatics servers that have the desired data. The individual informatics servers run in parallel, independently of each other.

Figure 6:
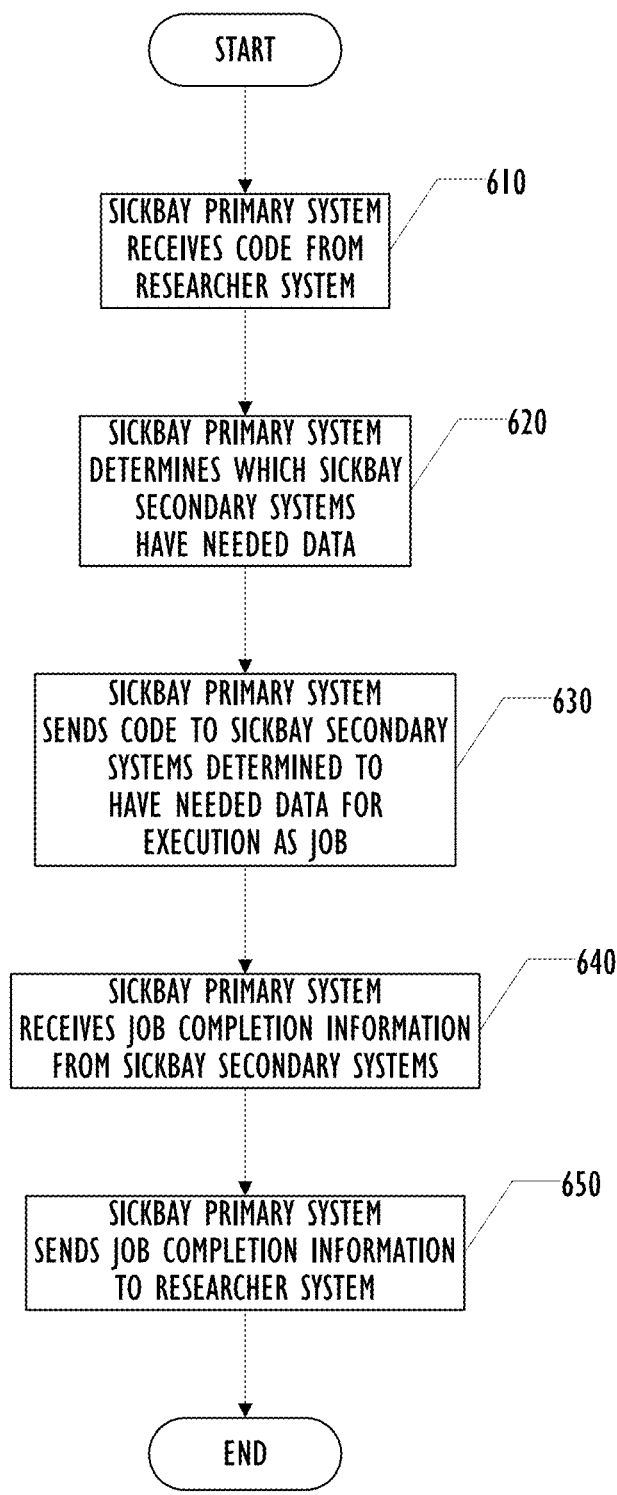
FIG. 6 is a flowchart illustrating a technique for performing rapid research in a hierarchy of distributed computing platforms according to one embodiment.

FIG. 6 is a flowchart illustrating a technique for a broader scale distributed machine learning according to one embodiment, using a hierarchy of Sickbay systems as described above. In block 610, a SICKBAY primary system receives code from the researcher's system. As described above, the code may be written in any programming language supported by the SICKBAY system, such as MATLAB or C. No changes are required to run the researcher's code. Instead of running the researcher's code on the SICKBAY primary system, the SICKBAY primary system in block 620 determines which SICKBAY secondary systems have data that is needed or relevant for running the code. Then in block 630 the SICKBAY primary system sends the code to the determined SICKBAY secondary systems as a job for execution by the SICKBAY secondary system on data maintained by the SICKBAY secondary system. Upon completion of the job by each SICKBAY secondary system, the SICKBAY primary system receives job completion information from the SICKBAY secondary system in block 640. In some embodiments, the job completion information may include updated model information or other non-PHI data generated as a result of running the researcher's code. Finally, in block 650, the SICKBAY primary system may send the job completion information to the researcher's system.

In some embodiments, the researcher's code may be sent out-of-band from the researcher's system to the secondary SICKBAY systems, and the SICKBAY primary system may take advantage of the prior distribution of the code and simply instruct the SICKBAY secondary systems to execute the code.

Although described in terms of healthcare organizations and PHI, the techniques and systems described above can be used in non-healthcare environments with any types of data that cannot be shared outside of an organization because of policy, regulatory, or statutory proscriptions.

While certain exemplary embodiments have been described in detail and shown in the accompanying drawings, it is to be understood that such embodiments are merely illustrative of and not devised without departing from the basic scope thereof, which is determined by the claims that follow.

We claim:

1. A system for hierarchical distributed machine learning, comprising:
 a plurality of secondary distributed computing systems, each associated with an organization of a plurality of organizations, each holding personal health information data that cannot be exported from the associated organization;
 a recording data collector system, outside of the plurality of organizations, programmed to aggregate job completion information received from the plurality of secondary distributed computing systems; and
 a primary distributed computing system, outside of the plurality of organizations, comprising:
 a primary compute job scheduler of a primary distributed computing system programmed to send compute jobs to each of the plurality of secondary distributed computing systems for execution on personal health information data held by the associated organization that cannot be exported from the associated organization,
 wherein each compute job exports job completion information to the recording data collector system, and
 wherein the job completion information comprises non-personal health information metadata calculated by the compute job.

2. The system for hierarchical distributed machine learning of claim 1, wherein each of the plurality of secondary distributed computing systems comprises:
   a plurality of informatics servers, each associated with a portion of the personal health information data held by the secondary distributed computing system;
   a job scheduler, programmed to:
      determine which of the plurality of informatics servers is associated with data needed by the compute job; and
      schedule execution of the compute job on informatics servers determined to be associated with data needed by the compute job.

3. The system for hierarchical distributed machine learning of claim 1, wherein the recording data collector system is the primary distributed computing system.

4. The system for hierarchical distributed machine learning of claim 1, wherein a secondary distributed computing system of the plurality of secondary distributed computing systems is a primary distributed computing system for a second plurality of secondary computing systems.

5. A system for distributed machine learning, comprising:
   a plurality of informatics servers, each associated with a corresponding database of personal health information data that is prohibited from being provided outside of an organization associated with that informatics server;
   a compute job for performing machine learning on one or more desired databases of personal health information data held by the plurality of informatics servers;
   a job scheduler, programmed to:
   determine a subset of the plurality of informatics servers is associated with a database of the one or more desired databases of data;
   send the compute job to the subset of the plurality of informatics servers;
   instruct the subset of the plurality of informatics servers to execute the compute job; and
   aggregate job completion information returned to the job scheduler from the compute job, wherein the job completion information is non-personal health information metadata calculated by the compute job.

6. The system of claim 5, wherein the compute job executes in parallel on the subset of the plurality of informatics servers.

7. The system of claim 5, wherein the compute job comprises code developed by a researcher on a researcher computer system that executes unchanged on the plurality of informatics servers.

8. The system of claim 5, wherein the corresponding database associated with each of the plurality of informatics servers comprises a collection of files, and
   wherein metadata about a meaning of each of the collection of files and a location of each of the collection of files is used by the job scheduler.

9. A method of performing distributed machine learning on restricted data, comprising:
   receiving at a primary distributed computing system a compute job for performing machine learning from a researcher computing system;
   determining which of a plurality of secondary distributed computing systems have data needed by the compute job, wherein each of the plurality of secondary distributed computing systems is associated with a different organization, wherein the primary distributed computing system is outside the organizations associated with the plurality of secondary distributed computing systems;
   sending the compute job to secondary distributed computing systems of the plurality of secondary distributed computing platforms systems determined to have the data needed by the compute job, wherein the data needed by the compute job is personal health information data that is restricted from being exported outside the associated organization;
   receiving by the primary distributed computing system job completion information from each of the secondary distributed computing platforms upon completion of the compute job, wherein the job completion information comprises non-personal health information metadata calculated by the compute job; and
   aggregating the job completion information received from each of the secondary distributed computing platforms.

10. The method of claim 9, further comprising:
    creating the compute job on the researcher computing system.

11. The method of claim 9, wherein receiving job completion information comprises receiving job completion information by a collecting and recording system.

* * * * *